US005620705A

United States Patent [19]
Dong et al.

[11] Patent Number: 5,620,705
[45] Date of Patent: Apr. 15, 1997

[54] PROGESTIN TABLET

[75] Inventors: Liang C. Dong, Mountain View; Patrick S.-L. Wong, Palo Alto; Steven Espinal, Sunnyvale, all of Calif.

[73] Assignee: ALZA Corporation, Palo Alto, Calif.

[21] Appl. No.: 441,889

[22] Filed: May 16, 1995

Related U.S. Application Data

[62] Division of Ser. No. 286,125, Aug. 4, 1994.

[51] Int. Cl.⁶ .............................. A61K 9/24; A61K 31/56
[52] U.S. Cl. ........................... 424/472; 424/473; 514/177
[58] Field of Search .................................. 424/472, 473; 514/177

[56] References Cited

U.S. PATENT DOCUMENTS

| | | | |
|---|---|---|---|
| 2,799,241 | 7/1957 | Wurster | 118/24 |
| 3,845,770 | 11/1974 | Theeuwes et al. | 128/260 |
| 3,916,899 | 11/1975 | Theeuwes et al. | 128/127 |
| 4,063,064 | 12/1977 | Saunders et al. | 219/121 L |
| 4,088,864 | 5/1978 | Theeuwes et al. | 219/121 |
| 4,327,725 | 5/1982 | Cortese et al. | 260/128 |
| 4,783,337 | 11/1988 | Wong et al. | 424/468 |
| 5,266,332 | 11/1993 | Dong et al. | 424/473 |

OTHER PUBLICATIONS

CA 118:45776, Wright et al., 1992.

*Primary Examiner*—Kimberly Jordan
*Attorney, Agent, or Firm*—Paul L. Sabatine; Mary Ann Dillahunty; Michael J. Rafa

[57] ABSTRACT

A hormone replacement composition, a hormone replacement dosage form, and a method of hormone replacement are disclosed and indicated for the management of hormone replacement therapy.

2 Claims, 5 Drawing Sheets

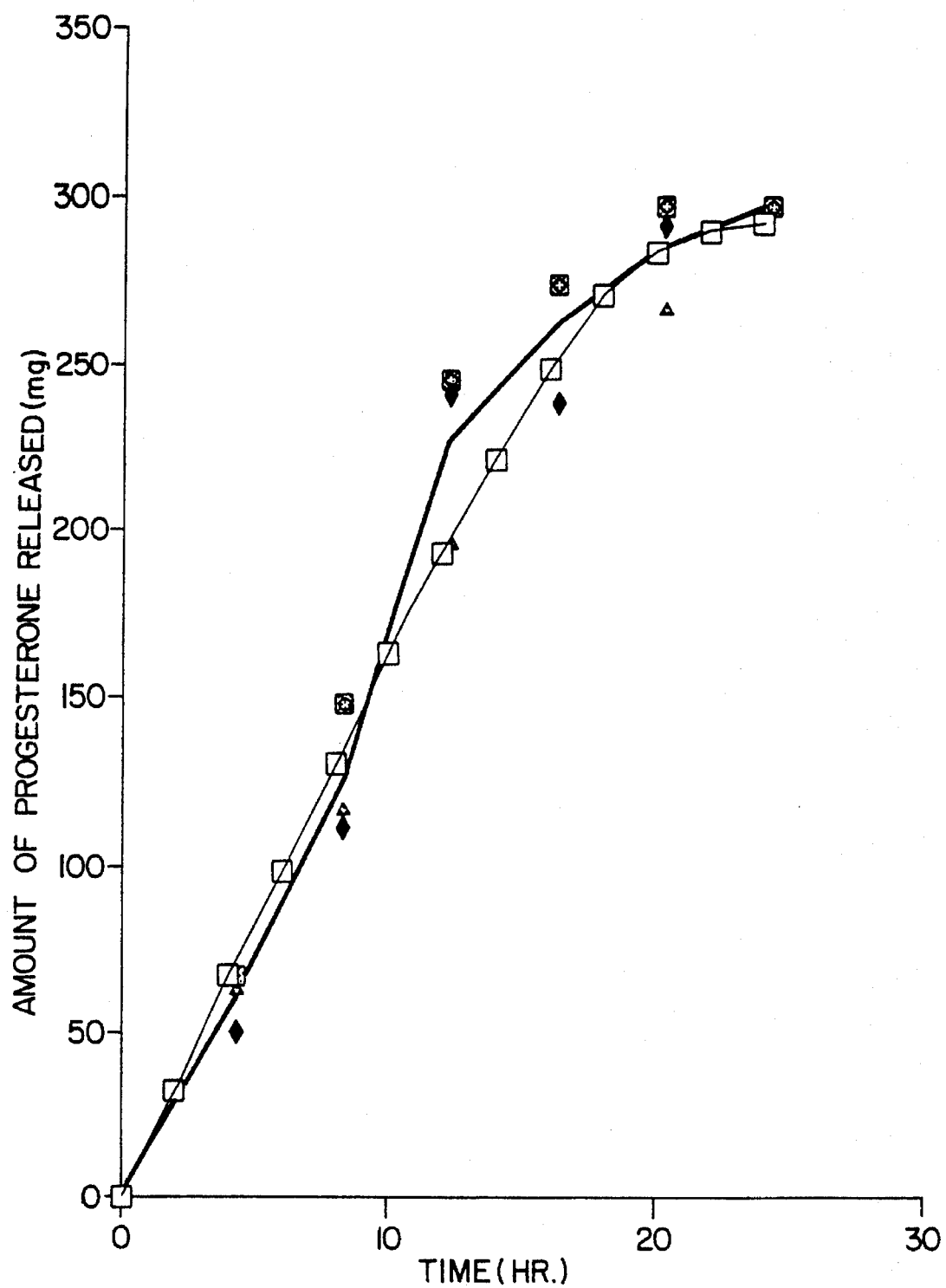
F I G. 1

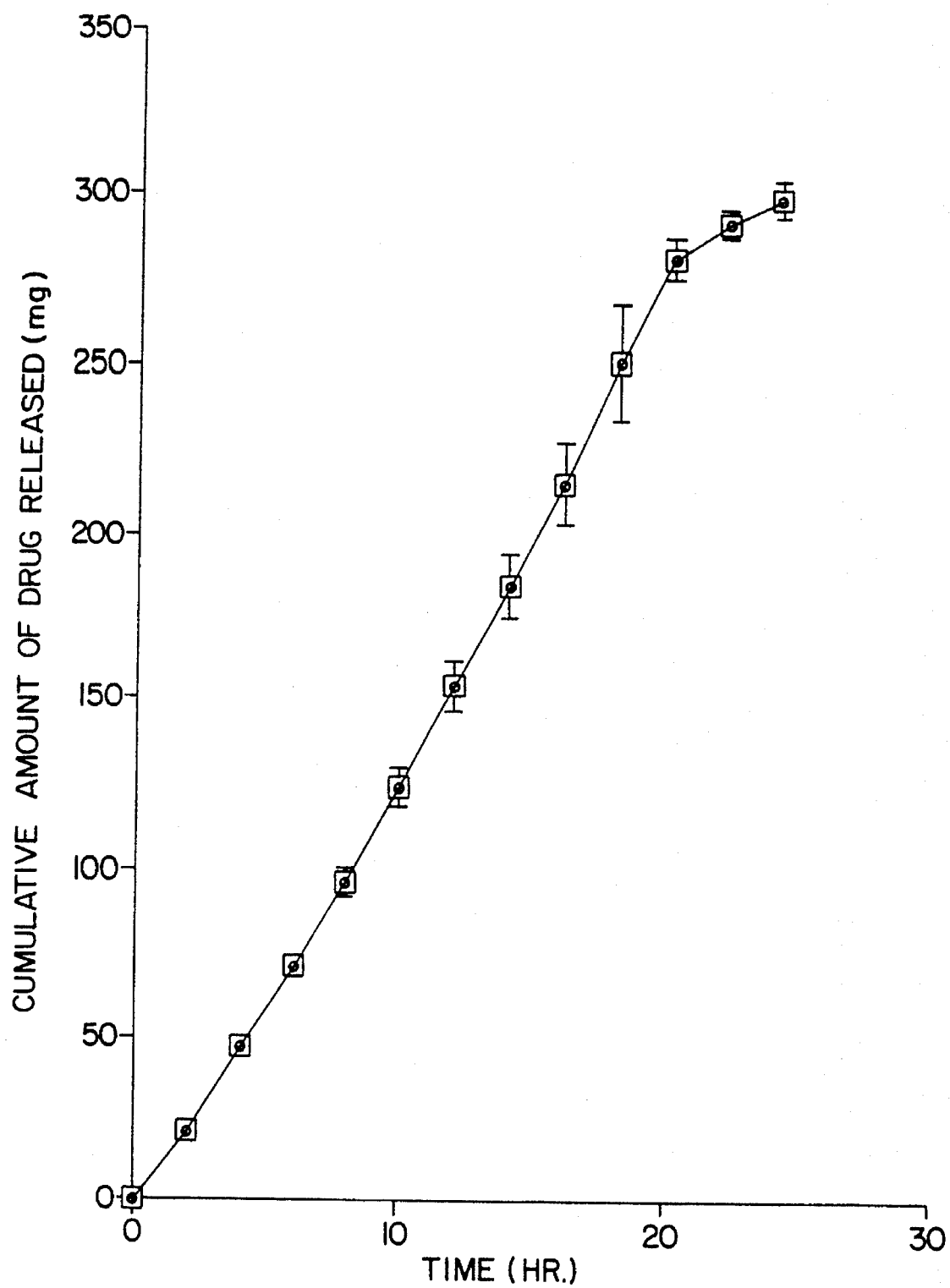
F I G. 2

PROGESTIN TABLET

This application is a division of application Ser. No. 08/286,125, filed Aug. 4, 1994, allowed not yet patented and benefit of the filing date of said earlier filed application is claimed under 35 U.S.C. § 120.

FIELD OF THE INVENTION

This invention pertains to a novel therapeutic composition comprising a progesterone. The invention concerns also a novel dosage form comprising a progesterone. The invention relates further to a method of progesterone replacement therapy by administering the composition, or by administering the dosage form for delivering progesterone for the indicated therapy.

BACKGROUND OF THE INVENTION

Progesterone is the active, natural progestin secreted by the ovary, mainly from the corpus luteum, from the placenta, and from the adrenal cortex. Progesterone released during the luteal phase of the normal female cycle leads to development of a secretary endometrium. Progesterone influences the endocervical glands, and progesterone is very important for the maintenance of pregnancy as progesterone suppresses menstruation and uterine contractility. Progesterone has application in the management of ovarian disorders, in dysfunctional irregular menstrual cycles, in dysmenorrhea, in premenstrual and post menopausal symptoms, especially in the latter where menopause is an endocrine deficiency state.

The medical and pharmaceutical prior arts administered progesterone as replacement therapy to provide progesterone for the physiological and therapeutic purposes indicated above, and more specifically for postmeno-pausal hormone replacement therapy. The medical and pharmaceutical prior arts administered progesterone for these therapies by injection with progesterone supplied in vegetable oil, progesterone in a suppository for vaginal or for rectal administration, progesterone in an intrauterine or vaginal device, and progesterone in a topical cream. The prior art dispensing of progesterone in oils, suppositories and creams lacked controlled delivery, and the prior art dispensing of progesterone in an intrauterine or vaginal device frequently lead to bleeding and infection of the uterus and the vagina. The prior art has not provided an acceptable oral means for administering progesterone at a controlled dose over time, even though patients are more comfortable taking compositions and dosage forms by mouth. The properties of progesterone are reported in *The Pharmacological Basis of Therapeutics*, by Gilman and Rall, 8th ed, pp 1384–1412 (1990), published by Pergamon Press, Inc.

SUMMERY OF THE INVENTION

In view of the foregoing presentation, it is immediately apparent a serious need exists for an improvement in the delivery of progesterone for hormone replacement therapy. The need exists for a novel therapeutic composition comprising progesterone for replacement therapy, and the need exists for a novel dosage form comprising progesterone for replacement therapy. Accordingly, it is an object of this invention to provide a therapeutic composition comprising progesterone and it is an object of the invention to provide a dosage form comprising progesterone, which are indicated for progesterone replacement therapy. It is additionally an object of this invention to provide a novel method of administering the composition comprising the progesterone for replacement therapy, and to a novel method of administering the dosage form for administering progesterone for replacement therapy. The invention provides an improvement in the administration of progesterone in comparison with intramuscular, vaginal, intrauterine and topical administration for progesterone replacement therapy.

BRIEF DESCRIPTION OF THE DRAWINGS

FIGS. 1 to 5 depict release patterns for compositions and dosage forms provided by the invention.

DESCRIPTION OF THE INVENTION

Figure 3:
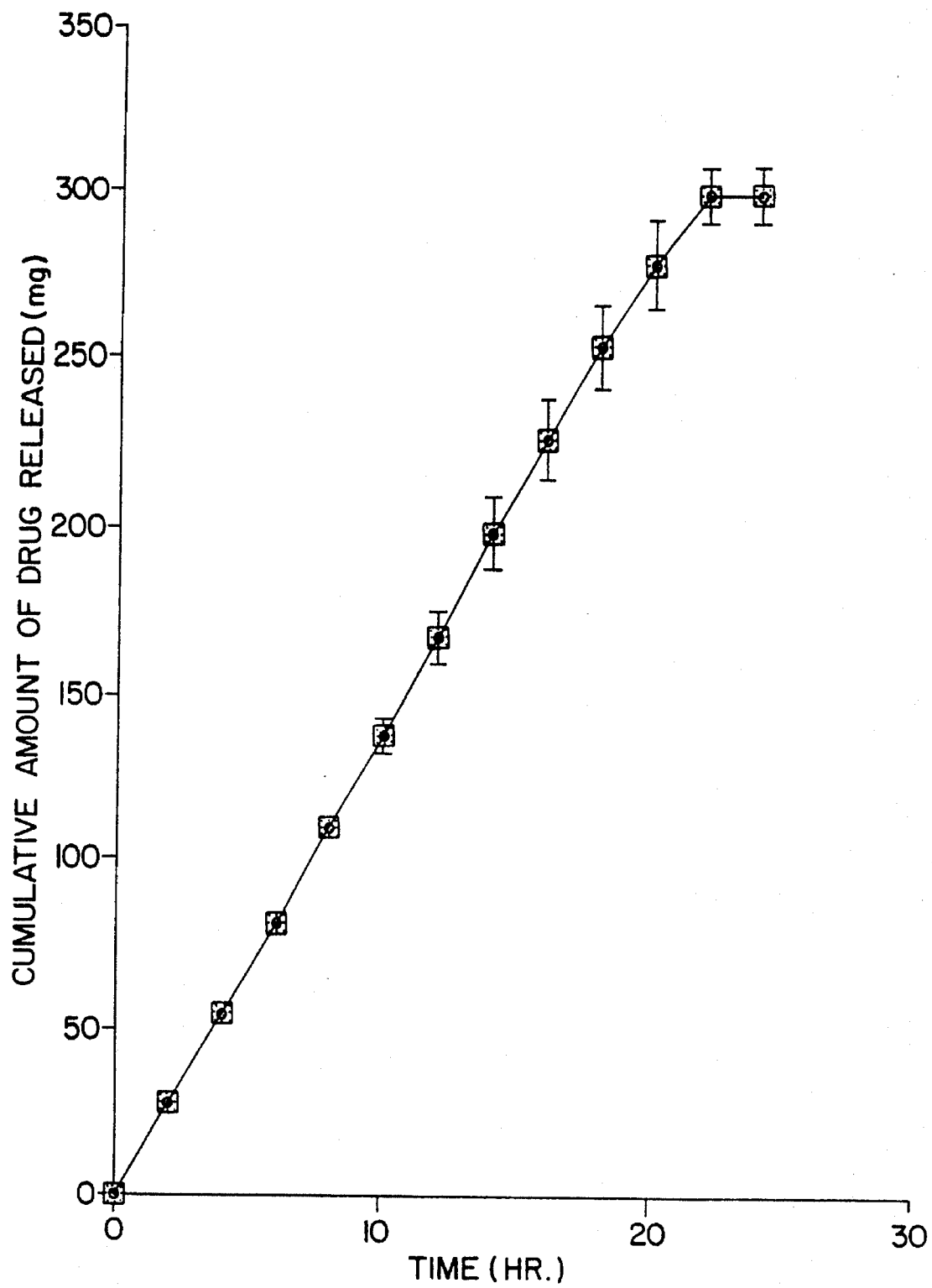

The drug progesterone, as used for the purpose of this invention refers to asteroid possessing hormone activity resembling the effects of natural progesterone. The progesterone that are clinically useful for this invention comprise (a) the naturally occurring 21-carbon steroid, specifically progesterone itself and 17-hydroxyprogesterone and their derivatives; (b) the 21-carbon progesterone derivatives, specifically medroxyprogesterone, and megestrol; and (c) the 19-nortestosterone and its derivatives such as norethindrone and norgestrel. Representative of steroids with progestational effects comprise a member selected from the group consisting of progestin, progestogen, medroxyprogesterone acetate, megestrol acetate, norethindrone, norethindrone acetate, norgestrel, hydroxyprogesterone caproate, norethisterone, norethisterone acetate, levonorgestrel, norgestimate, norethynodrel, 17-hyroxyprogesterone, 17-hydroxyprotesterone esters, 19-nor-17-hydroxyprogesterone, 19-nor-17-hydroxyprogesterone esters, 17α-ethinyltestosterone, 17α-ethinyl-19-nortestosterone, d-17β-acetoxy-13β-ethyl-17α-ethinyl-17β-hydroxygon-4-en-3-one, 13β-ethyl-17β-hydroxygon-4-en-3-one, 13β,17α-diethyl-17β-hydroxygon-4-en-3-one, chlormadione acetate, dimethistrone, 17α-ethinyl-β-acetoxy-19-norandrost-4-en-3 one oxime, 3-ketodesogestrel, desogestrel, gestodene, and gestodene acetate. The dose of progesterone and its derivative in a composition and in a dosage form is 10 ng to 1200 mg, that is administered over a period 30 hours for hormone replacement therapy, The following examples are illustrative of the invention and the examples should not be considered as limiting the invention in any way, as these examples and other equivalents thereof will be apparent to those versed in the art.

EXAMPLE 1

A therapeutic composition possessing the effects of progesterone for adjunctive hormone therapy is prepared as follows: first, in weight percent, 60% progesterone, 10% of cross-linked sodium carboxymethylcellulose of 250,000 molecular weight, 5% polyoxyethylene 40 stearate, 3.0% hydroxy-propylmethylcellulose of 11,200 molecular weight, and 21% mannitol are individually passed through a 40-mesh stainless steel screen, and then blended for 8 minutes in a standard blender. Next, dry ethanol is added slowly to the blending blender, and the blending continued to provide a wet blend of even consistency. The just prepared wet mass is passed through a 20-mesh screen and dried in an oven to granulation. Then, 1.0% magnesium stearate is added and blended to produce granules. The progesterone composition is compressed under 2.5 ton force into a flat tablet. A number of tablets prepared weigh 220 mg and comprised 132 mg of progesterone, 2.0 mg of cross-linked sodium carboxymethylcellulose, 11 mg of polyoxyethylene 40-stearate, 6.6 mg of hydroxypropylmethylcellulose, 46.2 mg of mannitol, and 2.2 mg of magnesium stearate. A number of tablets each weighing 280 mg are prepared comprising 168 mg of progesterone, 28 mg of cross-linked sodium carboxymethylcellulose, 14 mg of polyoxyethylene 40-stearate, 8.4 mg of hydroxypropylmethylcellulose, 58.8 mg of mannitol, and 2.8 mg of magnesium stearate. The therapeutic tablets provide controlled release hormone replacement therapy as the compressed tablet possess control over both the duration and the profile of the progesterone release curve.

EXAMPLE 2

The example described above is followed except that polyoxyethylene 40-stearate is replaced by a nonionic surface-active agent selected from the group consisting of sesquioleic acid sorbitan, trioleic acid sorbitan, monooleic acid sorbitan, monostearic acid sorbitan, monolauric acid sorbitan, monostearic acid polyethylene glycol, monoodeic acid polyoxyethylene-sorbitan, monolauric acid polyoxyethylene sorbitan, polyoxyethylenenonyl-phenyl ether, polyoxyethylenecetyl ether, polyoxyethylenelauryl ether, polyoxyethylene 50-stearate herein the polymer length is equivalent to about 50 oxyethylene units, polyoxyethylene 20-stearate, and a mixture of monostearate and distearate esters of polyoxyethylene diols of average polymer length of about 40 oxyethylene units. The concentration of surface active agent in the therapeutic composition is 1 mg to 30 mg.

EXAMPLE 3

The example described above is followed except that alkali carboxymethylcellulose is replaced by a polyalkylene oxide of 75,000 to 350,000 molecular weight as represented by a polyethylene oxide of 100,000 molecular weight, a polyethylene oxide of 200,000 molecular weight, and a polyethylene oxide of 300,000 molecular weight. The concentration of alkali carboxymethylcellulose or hydroxyporpylalkylcellulose in the therapeutic composition is 5 mg to 225 mg.

EXAMPLE 4

The example described above is followed except that the hydroxypropylmethylcellulose is replaced by a hydroxypropylalkylcellulose of 9,000 to 150,000 molecular weight as represented by a member selected from the group consisting of hydroxypropylmethylcellulose, hydroxypropylethylcellulose, hydroxypropylisopropylcellulose, hydroxypropylbutylcellulose, hydroxypropylpentylcellulose, and hydroxypropylhexylcellulose. The amount of hydroxypropylalkylcellulose present in the therapeutic composition is 0.05 mg to 20 mg.

EXAMPLE 5

The example described above is followed except that magnesium stearate is replaced by 0.01 mg to 7.5 mg of a lubricant selected from the group consisting of calcium stearate, sodium stearate, potassium oleate, stearic acid, sodium palmitate, magnesium oleate, and stearin.

EXAMPLE 6

The procedures of the above examples are followed except that hydroxypropylmethylcellulose is replaced by a dispersing agent that cooperates with the therapeutic composition to provide controlled disintegration of the compressed therapeutic progesterone tablet. The concentration of dispersing agent is 0.05 mg to 20 mg represented by a member selected from the group consisting of starches, clays, algins, gums, celluloses, crosslinked polymers, sodium starch glycolate, crosslinked polyvinylpyrrolidone, Veegum, bentonite, guar gum, carrageenan, soya, ion-exchange resins, crosslinked casein, and crospovidone.

EXAMPLE 7

A bilayer drug core for dispensing a progesterone to the gastrointestinal tract of a human in need of progesterone replacement therapy is manufactured as follows: first, a progesterone layer composition is prepared by blending in a mixer 60 wt % progesterone, 10.0 wt % sodium croscarmellulose of 250,000 molecular weight, 5.0 wt % polyoxyethylene 40 stearate, 3.0 wt % of hydroxypropylmethylcellulose of 9,200 molecular weight, and 21.0 wt % mannitol each are passed through a 40-mesh stainless screen and then blended for 7 to 10 minutes. Next, ethanol is added slowly to the mixer and mixing is continued to produce a wet mass. Then, the wet mass is screened through a 20-mesh screen and then dried in an oven at 50° C. until the granulation is dry. Next, 1.0 wt % magnesium stearate is added and blended to produce the progesterone granules.

Next, a displacement layer of the bilayer core is prepared by blending in a fluid-bed granulator 58.75 wt % sodium carboxymethylcellulose possessing a 700,000 molecular weight, 30.0 wt % sodium chloride, 5.0 wt % hydroxypropylmethylcellulose possessing a 11,200 molecular weight, and 1.0 wt % ferric oxide are each passed through a 40 mesh stainless steel screen, blended in the fluid-bed granulator and sprayed with a 5.0 wt % hydroxypropylcellulose possessing an 80,000 molecular weight in solution in distilled water to provide homogenous granules. The granules are passed through an 8 mesh stainless steel screen and then mixed with 0.25 wt % magnesium stearate. The progesterone granules are pressed into a tablet-shaped layer and the displacement granules are pressed into a corresponding tablet-shaped layer using a 17/64 inch (7 mm) punch. Next, the displacement tablet layer is placed into the bottom of a gelatin capsule and the progesterone tablet layer is placed into the gelatine capsule distant from the bottom of the capsule and in contacting layer to provide a bilayer core. The capsule is closed with the top of the capsule to provide a gelatin capsule comprising the bilayer core.

EXAMPLE 8

The procedure in Example 7 is repeated with the progesterone-layer forming composition comprising an alkali carboxymethylcellulose wherein the alkali is a member selected from the group consisting of sodium and potassium and the alkali carboxymethylcellulose has a molecular weight of 75,000 to 350,000; and the displacement layer comprises an alkali carboxy-methylcellulose comprises a 500,000 to 1,000,000 molecular weight.

EXAMPLE 9

The procedure of Example 7 is followed to provide a displacement layer comprising 50 mg to 200 mg of alkali carboxymethylcellulose, 25 mg to 125 mg of an osmotically effective solute, 1 mg to 20 mg of hydroxy-propylmethylceilulose, encased with 1 mg to 20 mg of hydroxypropylcellulose, as exemplified by a displacement composition comprising 146 mg of sodium carboxymethylcellulose, 75 mg of sodium chloride, 12.5 mg of hydroxypropylmethylcellulose, and 0.625 mg of magnesium stearate, encased with 12.5 mg of hyroxypropylcellulose.

EXAMPLE 10

The procedure of Example 7 is followed with the alkali carboxymethylcellulose of the displacement composition replaced by a poly(alkylene oxide) of 3,000,000 to 7,500,000 molecular weight as represented by poly(ethylene oxide).

EXAMPLE 11

The capsule comprising the bilayer core prepared according to Example 7, which capsule comprises an interior surface facing the bilayer core, and an exterior surface, is coated on its exterior surface with a semipermeable wall. the semipermeable wall forming composition comprises 85 wt % cellulose acetate having an acetyl content of 39.8% and 15 wt % polyethylene glycol having a 3,350 molecular weight. The wall-forming composition is dissolved in acetone-methanol mixed solvent 80/20, wt/wt, to make a 4% solid solution. The wall forming composition is sprayed onto the capsules in a coater. The semipermeable wall weighs about 105 mg. Finally, an exit orifice, 155 mil(mm) is drilled through the semipermeable wall to connect the progesterone layer with the exterior of the dosage form after the capsule wall dissolves in a body fluid. The residual solvent is removed by drying at 50° C. and 50% humidity for 3 days. The final dosage form delivers progesterone in vitro, or in vivo in dogs, at an average rate of 15 mg/hour with 90% of the progesterone released at a controlled rate in 18 hours, as seen in FIG. 1. In FIG. 1, the release profile of a dosage form comprising progesterone is plotted for three dogs, the checkered square is dog 1, the black diamond is dog 2, and the triangle is dog 3, the solid black line is the in-vivo average and the clear squares is the lot clearance (in-vitro).

EXAMPLE 12

The procedure of Examples 7 and 11 are followed for providing drug-progesterone layer composition weighing 500 mg and a displacement layer weighing 250 mg, the bilayers tablets are coated with a subcoat composition. The subcoat is an inner coat in contact with the bilayer coat. The subcoat composition weighed 33 mg and the subcoat comprises 50% hydroxypropyl-methylcellulose possessing a 11,900 molecular weight ad 50% hydroxy-propylcellulose possessing a 80,000 molecular weight. The subcoat is coated with an outer overcoat a semipermeable wall comprising cellulose acetate and polyethylene glycol. An orifice is drilled through the semi-permeable overcoat to provide a release profile of progesterone as seen in FIG. 2.

EXAMPLE 13

The procedure of Example 12 is followed to provide the dosage form wherein the subcoat comprises 100% hydroxyethylcellulose possessing a 90,000 molecular weight. The subcoat is coated with a semipermeable outer coat and an orifice drilled in the dosage form as described previously. In accompanying FIG. 3, the release profile of progesterone is plotted for the dosage form comprising the subcoat hydroxyalkylcellulose.

EXAMPLE 14

The above procedures are followed to provide a dosage form comprising a semipermeable wall wherein the wall comprises a member selected from the group consisting of a cellulose ester, cellulose diester, cellulose triester, cellulose ether, cellulose ester-ether, cellulose acylate, cellulose diacylate, cellulose triacylate, cellulose acetate, cellulose diacetate, and cellulose triacetate.

EXAMPLE 15

The above procedures are followed to provide a dosage form comprising an osmagent, also known as an osmotically effective solute, and as an osmotic agent as represented by a member selected from the group consisting of magnesium sulfate, sodium chloride, lithium chloride, potassium sulfate, sodium sulfate, lithium sulfate, potassium acid phosphate, mannitol, urea, inositol, magnesium succinate, tartaric acid, carbohydrates like raffinose, sucrose, glucose, lactose, fructose, mixture of sodium chloride, a mixture comprising potassium chloride and dextrose, and a mixture of potassium chloride and sodium chloride. The amount of osmagent in the drug composition is 0.5 mg to 75 mg, and the amount of osmagent in the displacement composition is 0.5 mg to 100 mg.

EXAMPLE 16

Exemplary solvents used for the present examples comprise inorganic and organic solvents that do not adversely harm the materials and the final wall or the final compositions in the dosage form. The solvents broadly include member selected from the group consisting of aqueous solvents, alcohols, ketones, esters, ethers, aliphatic hydrocarbons, halogenated solvents, cycloaliphatics, aromatics, heterocyclic solvents, and mixtures thereof. Typical solvents include acetone, diacetone, alcohol, methanol, ethanol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, chloroform, nitroethane, nitropropane, tetrachloroethane, ethyl ether, isopropyl ether, cyclo-hexane, cyclo-octane, benzene, toluene, naphtha, 1,4-dioxane, tetrahydrofuran, diglyme, aqueous and nonaqueous mixtures thereof, such as acetone and water, acetone and methanol, acetone and ethyl alcohol, methylene dichloride and methanol, and ethylene dichloride and methanol.

EXAMPLE 17

In the proceeding examples, the expression, "exit means", as used for the dosage form of this invention, comprises means and methods suitable for the metered release of beneficial drug progesterone from the dosage form. the exit means comprises at least one passageway, orifice, or the like, through the wall for communicating with progesterone in the dosage form. The expression, "at least one passageway", comprises aperture, orifice, bore, pore, porous element through which the progesterone can migrate, hollow fiber, capillary tube, porous overlay, porous insert, and the like. The expression also includes a material that erodes or is leached from the wall in the fluid environment of use to produce at least one passageway in the dosage form. Representative materials suitable for forming at least one passageway, or a multiplicity of passageways, include an erodible poly(glycolic) acid, or poly(lactic) acid member in the wall, a gelatinous filament, poly(vinyl alcohol), leachable materials such as fluid removable pore forming polysaccharides, salts, oxides, or the like. A passageway or a plurality of passageways can be formed by leaching a material such as sorbitol, lactose, fructose and the like from the wall. The passageway can have any shape such as round, triangular, square, elliptical, and the like, for assisting in the metered release of morphine from the dosage form. The dosage form can be constructed with one or more passageways in spaced apart relations, or more than one passageway on a single surface of a dosage form. Passageways and equipment for forming passageways are disclosed in U.S. Pat. Nos. 3,845,770; 3,916,899; 4,063,064 and 4,088,864. Passageways of given size formed by leading are disclosed in U.S. Pat. Nos. 4,200,098 and 4,285,987.

EXAMPLE 18

The procedure of the above examples are followed to provide a theupeutic composition for use in a method for orally administering progestin for providing a progestin pattern, consisting of a blood level of 2 ng/ml to 20 ng/ml in the blood of a human.

DISCLOSURE FOR USING THE INVENTION

The invention concerns a method for administering progesterone for hormone replacement therapy 10 ng to 1200 mg over a period of 30 hours. The method, in one administration comprises admitting orally into the patient 10 ng to 1200 mg of a progesterone or a progesterone active compound, that is administered from a therapeutic composition as a controlled hormone replacement dose for the intended effect.

The method concerns also a method for administering 10 ng to 1200 mg of progesterone, or a therapeutically-equivalent progesterone-like hormone, by admitting orally into the patient a dosage form comprising a semipermeable wall permeable to aqueous-biological fluid and impermeable to the passage of progesterone and hormones possessing progesterone activity, which wall surrounds a member selected from the group consisting of a capsule and a hydroxyalkylcellulose to define an internal compartment, which compartment comprises a progesterone layer and a displacement-push layer and with an exit means for delivering the progesterone from the dosage form. The dosage form delivers the progesterone by imbibing fluid through the semipermeable wall into the dosage form causing the progesterone to change from a resting state to a dispensable state, and the displacement push composition to expand and push the progesterone composition through the exit, whereby through the combined operations of the dosage form, the hormone replacement therapy is affected at a dose controlled rate over a sustained period of time.

Figure 4:
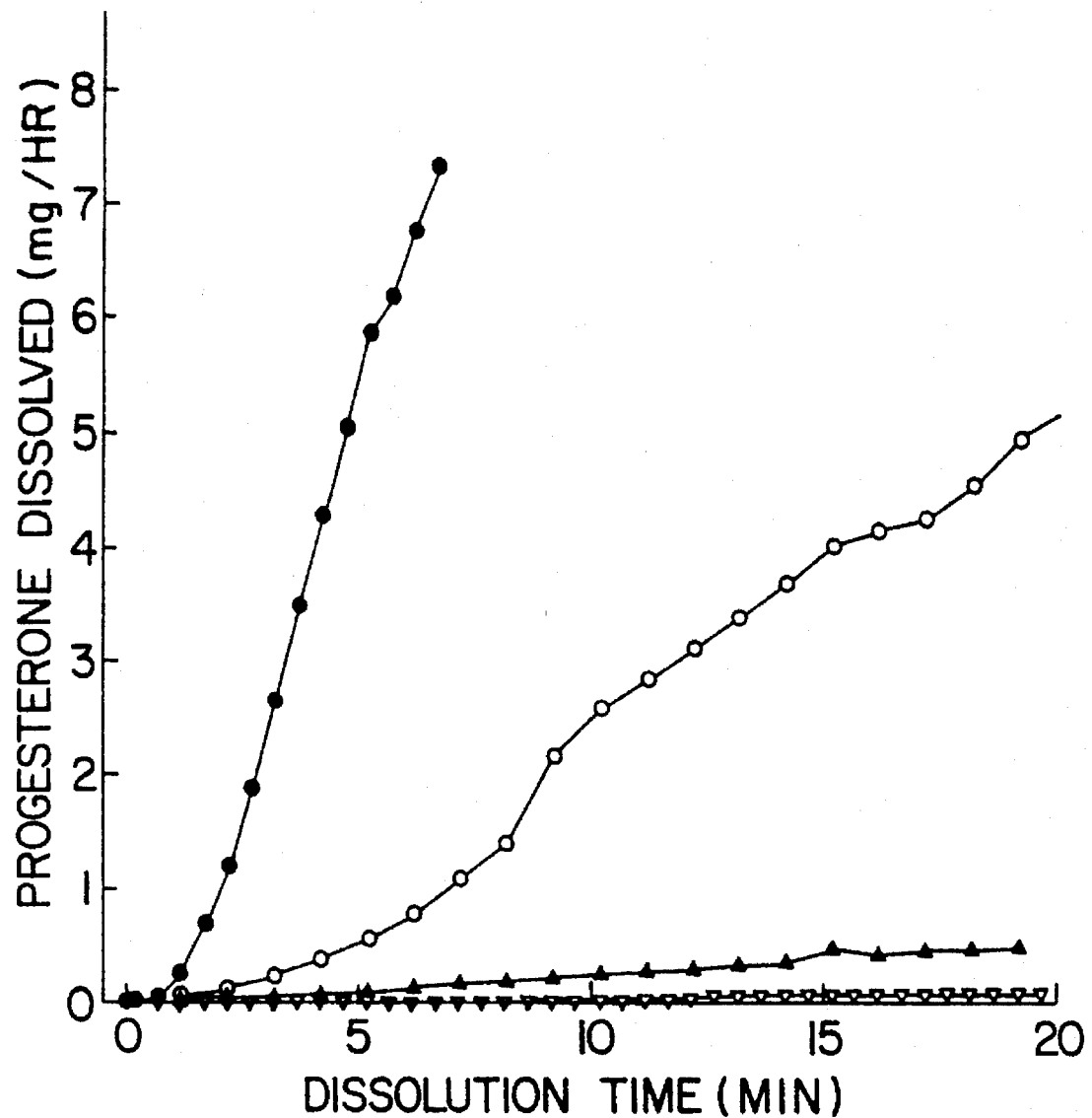
Figure 5:
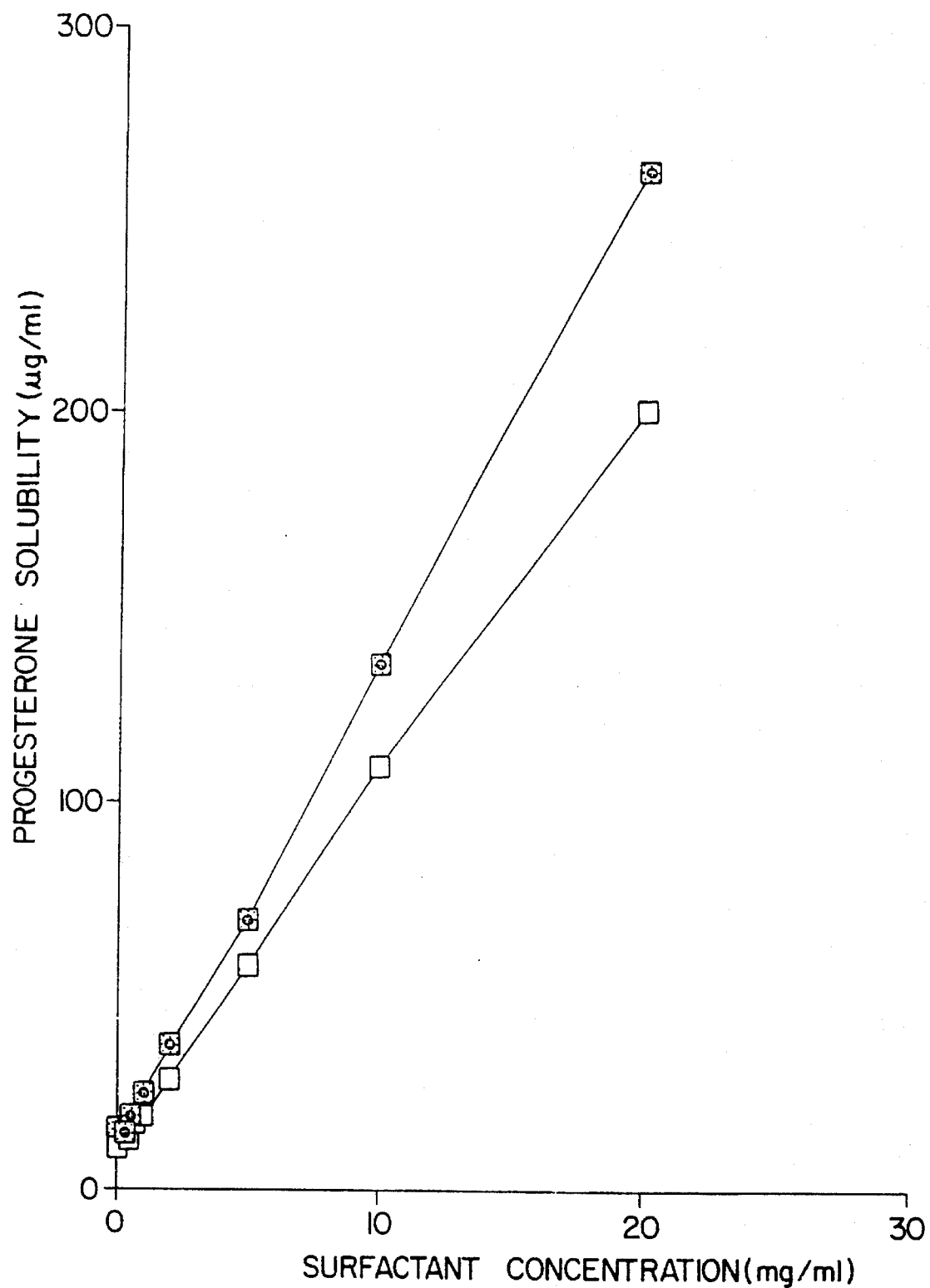

The dosage forms of this invention provide unexpected results as seen in the accompanying FIGS. 4 and 5. FIG. 4 shows the progesterone dissolution in deionized water and various formulations. In FIG. 4, all the tablets comprise 80% progesterone and 0.5% magnesium stearate. The tablets comprising both surfactant polyoxyethylene 40 stearate and polyvinylpyrrolidone comprised 10% polyvinylpyrrolidone XL and 9.5% polyethylene 40 stearate. In additional tablets, the disintegrant polyvinylpyrrolidone and/or the surfactant polyoxyethylene 40 stearate with mannitol. The tablets weighed 125 mg and were made with a ¼ inch (7.5 mm) tool. The tablets were tested in a USP bath with 900 ml of 37° C. artificial intestinal fluid and 50 rpm stirring, with filters used to eliminate light scattering from undissolved particles. In FIG. 4, the clear triangles indicate tablets made free of both surfactant and disintegrant; the dark triangles indicate tablets comprising surfactant and free of disintegrant; the clear circles indicates tablets comprising disintegrant and free of surfactant and the dark circles denotes tablets comprising both surfactant and disintegrant. The results of FIG. 4 show that surfactant and the disintegrant had a synergetic effect on the progesterone dissolution that is essential to the bioavailability of a hydrophobic drug like progesterone. The combined functions of the disintegrant and the surfactant is for the disintegrant to dissipate or break down the drug-layer or tablet rapidly after it is dispensed from the dosage form, and in accompanying FIG. 5, the function of the surfactant is to increase the solubility in the environment of use, a patient. The accompanying FIG. 5, depicts the solubility of progesterone in water as a function of surfactant concentration, as measured for polyoxyethylene 40 stearate at 25° C. expressed by clear squares, and at 37° C. as expressed by hatched squares.

Inasmuch as the foregoing specification comprises disclosed embodiments, it is understood that variations and modifications may be made, in accordance with the principles disclosed, without departing from the invention.

We claim:

1. A therapeutic bilayer tablet for hormone replacement therapy, wherein the bilayer comprises a drug layer comprising 60 wt % progesterone, 10.0 wt % sodium croscarmellose, 5.0 wt % polyethylene 40 stearate, 3.0 wt % hydroxypropylmethylcellulose and 21 wt % mannitol; and a displacement layer comprising 58.75 wt % sodium carboxymethylcellulose, 30 wt % sodium chloride, and, 5.0 wt % hydroxypropylethylcellulose.

2. A therapeutic bilayer tablet for hormone replacement therapy, wherein the bilayer comprises a drug layer comprising 10 ng to 1200 mg of a progestin, 1 mg to 30 mg of a surfactant, 5 mg to 225 mg of an alkali carboxymethylcellulose possessing a 75,000 to 350,000 molecular weight, 0.05 ng to 20 mg of a disintegrant, and 0.5 mg to 75 mg of an osmagent; and a displacement layer comprising 50 mg to 200 mg of an alkali carboxymethylcellulose of 500,000 to 1,000,000 molecular weight, 1 mg to 20 mg of hydroxypropylmethylcellulose of 9,000 to 150,000 molecular weight and 0.5 mg to 100 mg of an osmagent.

* * * * *